United States Patent [19]
Deboeck et al.

[11] Patent Number: 5,288,505
[45] Date of Patent: Feb. 22, 1994

[54] EXTENDED RELEASE FORM OF DILTIAZEM

[75] Inventors: Arthur M. Deboeck, Gurabo, P.R.; Philippe R. Baudier, Waterloo, Belgium

[73] Assignee: Galephar P.R., Inc., Ltd., Carolina, P.R.

[21] Appl. No.: 721,396

[22] Filed: Jun. 26, 1991

[51] Int. Cl.$^5$ .................. A61K 9/16; A61K 9/58
[52] U.S. Cl. .................. 424/497; 424/457; 424/458; 424/462; 424/490; 424/499; 424/502
[58] Field of Search .............. 424/499, 457, 458, 462, 424/490, 493, 498, 497

[56] References Cited

U.S. PATENT DOCUMENTS

| | | | |
|---|---|---|---|
| 3,964,255 | 6/1976 | Catanzarite | 60/205 |
| 4,263,273 | 4/1981 | Appelgren et al. | 424/21 |
| 4,556,925 | 12/1985 | Suenaga et al. | 360/113 |
| 4,600,645 | 7/1986 | Ghebre-Sellassie et al. | 428/403 |
| 4,623,588 | 11/1986 | Nuwayser et al. | 424/31 |
| 4,705,695 | 11/1987 | Lehmann et al. | 424/19 |
| 4,721,619 | 1/1988 | Panoz et al. | 424/468 |
| 4,784,858 | 11/1988 | Ventouras | 424/468 |
| 4,808,413 | 2/1989 | Joshi et al. | 424/489 |
| 4,824,678 | 4/1989 | Lindahl et al. | 424/473 |
| 4,832,958 | 5/1989 | Baudier et al. | 424/473 |
| 4,839,177 | 6/1989 | Colombo et al. | 424/482 |
| 4,859,469 | 8/1989 | Baudier et al. | 424/462 |
| 4,891,230 | 1/1990 | Geoghegan et al. | 424/461 |
| 4,894,240 | 1/1990 | Geoghegan et al. | 424/497 |
| 4,917,899 | 4/1990 | Geoghehan et al. | 424/461 |
| 4,938,967 | 7/1990 | Newton et al. | 424/458 |
| 4,952,402 | 8/1990 | Sparks et al. | 424/419 |
| 4,960,596 | 10/1990 | Debregeas et al. | 424/459 |
| 5,000,962 | 3/1991 | Sangekar et al. | 424/482 |
| 5,002,776 | 3/1991 | Geoghegan et al. | 424/497 |
| 5,051,262 | 9/1991 | Panoz et al. | 424/468 |
| 5,175,003 | 12/1992 | Goldman | 424/484 |

FOREIGN PATENT DOCUMENTS

| | | |
|---|---|---|
| 0149920A2 | 12/1984 | European Pat. Off. |
| 0322277A1 | 12/1988 | European Pat. Off. |
| 0340105A1 | 4/1989 | European Pat. Off. |
| 0373417A1 | 11/1989 | European Pat. Off. |

Primary Examiner—Thurman K. Page
Assistant Examiner—James M. Spear
Attorney, Agent, or Firm—Oblon, Spivak, McClelland, Maier & Neustadt

[57] ABSTRACT

An extended-release galenical form of Diltiazem or a pharmaceutically acceptable salt thereof, which comprises beads containing said Diltiazem or a pharmaceutically acceptable salt thereof as an active ingredient and a wetting agent, said beads being coated with a microporous membrane comprising at least a water-soluble or water-dispersible polymer or copolymer and a pharmaceutically acceptable adjuvant.

15 Claims, 2 Drawing Sheets

EXTENDED RELEASE FORM OF DILTIAZEM

BACKGROUND OF THE INVENTION

1. Field of the Invention

The present invention relates to an extended release form of Diltiazem, a process for the manufacture thereof and pharmaceutical compositions containing the same.

2. Description of the Background

Diltiazem hydrochloride is used in medicine principally for its calcium channel blocking properties, and, therefore, finds application in the treatment of angina pectoris and hypertension; either alone or in combination with other medications.

Although the mechanism for calcium channel blocking is not completely understood, calcium ion entry is believed to be inhibited through select voltage, with the sensitive areas termed "slow channels", across cell membranes. By reducing intracellular calcium concentration in cardiac and vascular smooth muscle cells, coronary arteries, peripheral arteries and arterioles are dilated and heart rate may be reduced. Also, myocardial contractibility may be decreased and atrioventricular nodal conduction may be slowed. The activity of diltiazem in human is directly related to its blood or plasma concentration.

For illnesses which require continuous and constant control, such as hypertension and angina pectoris, Diltiazem must be administered every 6 to 8 hours, as it has a very short half-life in blood of only about 3 to 4 hours. However, such frequent administration times render the treatment very annoying or even impossible to effect, particularly during the night. Further, after each administration of an immediate-release galenic form of Diltiazem, which generally is necessary four times per day, a succession of rapidly increasing and decreasing plasmatic Diltiazem concentrations are established. Thus, the organism being treated and the target organ, more particularly the heart, are alternatively subjected to overdoses and to underdoses of medicine.

In order to alleviate these drawbacks, a first galenic form of sustained-released of Diltiazem known under the trade name CARDIZEM SR ® was developed and presented in the form of "erodible pellets", U.S. Pat. No. 4,721,619. Although this form affords a reduction in peak concentration and in the number of daily intakes from 4 to 2, it does not eliminate high Diltiazem blood concentration between successive medication intakes. Hence, the patient is still obliged to take the medication twice daily. The products as described in U.S. Pat. No. 4,721,619 are prepared by a building up process which requires, as described therein, between 50 and 200 layers so as to obtain a core which, thereafter, requires between 20 and 40 layers of coating so as to obtain the membrane. Moreover, the solvent of the polymer solution used to make the membrane is constituted by organic solvents, such as isopropanol, methanol, acetone, and methylene chloride which are dangerous to use due to their flammability and toxicity. Such solvents are also environmentally hazardous. Particular care must be taken to avoid any traces of solvent in the final product because these solvents are toxic and are unsuitable in the product which is administered orally.

Thus, a need continues to exist for a multiple unit extended-release diltiazem hydrochloride galenical form which need be administered only once daily, and from which blood Diltiazem concentrations are not effected by the concomitant intake of food, and, further, which can be made by a process not using organic solvents.

SUMMARY OF THE INVENTION

Accordingly, it is an object of the present invention to provide galenic forms of Diltiazem with extended release of the active substance.

It is also an object of this invention to provide galenic forms of Diltiazem having excellent bioavailability while avoiding plasmatic concentration peaks.

The above objects and others which will become more apparent in view of the following disclosure are provided by an extended-release galenical form of a pharmaceutically acceptable salt of Diltiazem, which comprises beads containing the pharmaceutically acceptable salt of Diltiazem as an active ingredient and a wetting agent, said beads being coated with a microporous membrane comprising a water-soluble or water-dispersible polymer or copolymer, and a pharmaceutically acceptable adjuvant.

DETAILED DESCRIPTION OF THE PREFERRED EMBODIMENTS

Figure 1:
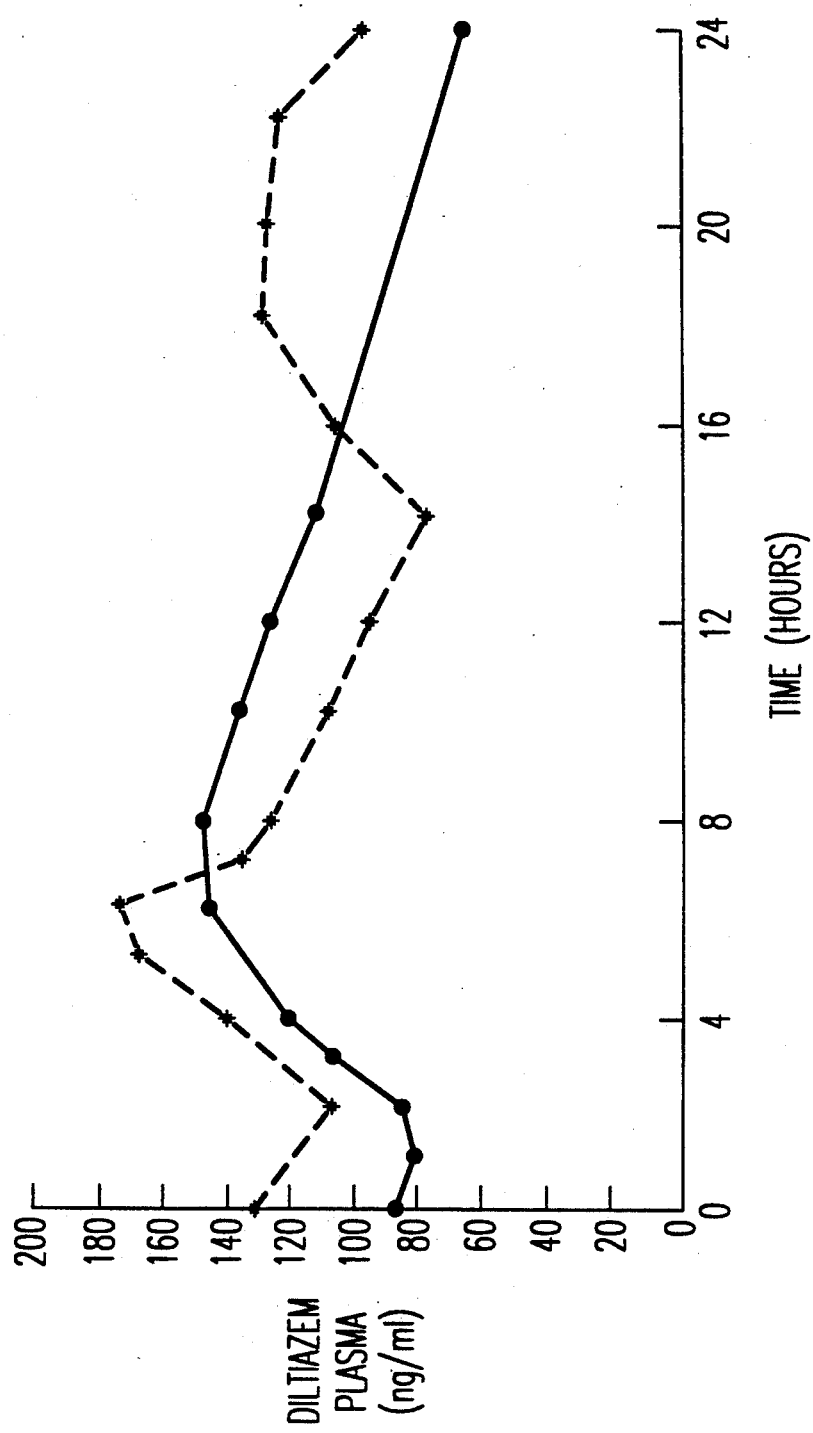
FIG. 1 illustrates the effect of the present invention in gradually releasing Diltiazem in a relatively uniform manner over a period of about one day after the 8th once daily administration in comparison with the effect of a conventional product after the 8th day of administration twice daily.

Diltiazem or (2S-cis)-3-(Acetyloxy)-5-[2-(dimethylamino)ethyl]-2,3-dihydro-2,(4-methoxyphenyl)-1,5-benzothiazepin-4(5H) has been known for more than 20 years. The synthesis thereof is described in German patent 1,805,714, corresponding to U.S. Pat. No. 3,562,257.

The present invention relates to novel galenic forms of Diltiazem being characterized by having an extended-release of the active substance. These galenic forms afford excellent bioavailability while avoiding plasmatic concentrations peaks, so that it is now possible to maintain diltiazem plasmatic concentrations in a desired, effective range while simplifying the administration of the medicine to only once daily.

According to the present invention, the Diltiazem extended release galenic forms are substantially characterized by the fact that they are constituted by beads containing a pharmaceutically acceptable salt of Diltiazem as an active substance, associated with at least a wetting agent, the beads being covered with a microporous membrane constituted by at least a water-soluble or water-dispersible polymer or copolymer such as a copolymer of acrylic acid ethyl ester and acrylic acid methyl ester, and a pharmacologically acceptable adjuvant.

In accordance with the present invention, any pharmaceutically acceptable salt of Diltiazem may be prepared in extended release form. For example, such salts may include the hydrochloride, sulfate or phosphate salts. However, they may also include the acetate, citrate or lactate salts, for example. It is preferred however, that the hydrochloride salt be used.

In more detail, the microporous membrane whereof the Diltiazem containing microgranules are covered, is constituted by a mixture of a water-soluble and/or water-dispersible copolymer and including at least one adjuvant which may be plastifying agents, pigments, fillers, wetting agent lubricants and antifoam agents.

The active substance containing beads are presented in form of spherules the diameter of which is between about 0.05 mm and 3 mm, preferably between about 0.1 mm and 2 mm.

Among the wetting agents associated with the Diltiazem or salt thereof in the beads, the following compounds may more particularly be exemplified:

sugars, for example saccharose, mannitol, sorbitol and lactose;

lecithins;

$C_{12}$ to $C_{20}$ fatty acid esters of saccharose, commercialized under the name of sucroesters (Gattefosse, France) or under the name of crodesters (Croda, U.K.);

xylose esters or xylites;

polyoxyethylenic glycerides;

esters of fatty acids and polyoxyethylene (Brijs, Renex and Eumulgines, Henkel, RFA);

sorbitan fatty acid esters (Span, Atlas, U.S.A.);

polyglycides-glycerides and polyglycides-alcohols esters (Gelucires, Gattefosse, France).

In addition to at least one of the above named wetting agents the beads may contain excipients or carriers, such as: Microcrystalline celluloses, such as Avicel products (FMC, U.S.A); methylcelluloses, carboxymethylcelluloses, hydroxyethylcelluloses (Natrosol, Hercules, U.S.A.), hydroxypropyl celluloses (Klucels, Hercules, U.S.A.); and starches.

Among the water-soluble and/or dispersible film forming polymers or copolymers constituting the microporous membrane, may be mentioned particularly polyacrylates and polymethacrylates of the Eudragit type, such as Eudragit E30D, L30D, RS - 30 D of Röhm Pharma (RFA), ethylcelluloses, such as Ethocels of DOW, U.S.A. and such as AquaCoat of FMC, U.S.A., Hydroxypropyl cellulose and hydroxypropylmethylcellulose and their derivations.

These polymers or copolymers may be associated into the microporous membrane with at least one adjuvant as exemplified by the following:

plastifying agents, such as triacetin, dibutylphthalate, dibutylsebacate, citric acid esters, polyethyleneglycols, polypropyleneglycols and polyvinylpyrrolidone;

pigments, such as iron oxides and titanium oxide;

fillers, such as lactose and sucrose;

wetting agents, such as surfactive agents of the Span and Tween types, namely partial esters of fatty acids (lauric, palmitic, stearic and oleic acids) and anhydrides of hexitols derived from sorbitol possibly containing polyoxyethylenic chains, preferably surfactive agents of the Tween type, namely Tween 80, as well as polyethyleneglycols;

lubricants, such as magnesium stearate and talc;

antifoaming agents, such as silicone oil.

In addition to the polymer or copolymer, the microporous membrane contains, preferably, talc and/or magnesium stearate as a lubricant, polyvinylpyrrolidone as a plastifying agent, titanium dioxide as a pigment, Tween 80 as an emulsifier, and silicone oil as an antifoaming agent.

Generally, the thickness of the microporous membrane is expressed by the percentage of the coating applied to the uncoated beads.

The weight of the microporous membrane may be 2 to 35%, preferably, 5 to 22%, of the weight of said microgranules. These beads may contain the Diltiazem salt in an amount of 20 to 95% by weight, preferably 30 to 85% by weight. The microporous membrane may contain 5 to 95% and, preferably, 30 to 90% of polymers, polymer mixture or copolymers.

The invention relates also to a medicine containing Diltiazem or salt thereof for extended release, the medicine being constituted by beads containing the Diltiazem or salt, such as the hydrochloride, and at least a wetting agent, coated with at least one polymer-based microporous membrane, the coated beads being contained in capsules, little bags or dosage dispensers.

The present invention relates also to a process for obtaining novel forms of a Diltiazem or salt thereof having extended-release in the gastro-intestinal tract, said process entailing preparing beads and coating the salt with a single microporous membrane.

The beads of the Diltiazem or salt thereof may be prepared using a conventional technique. A first technique consists in mixing the Diltiazem or salt thereof with the wetting agent(s) in a melted or finely divided form, or in solution, in the presence of a solvent, such as water, so as to obtain an extrudable paste or plastic mass. Said paste is thereafter extruded in an extruder and then rendered spherical. Several extruder types are usable, for example the extruder of ALEXANDER WERK (RFA) or the apparatus called X-truder of FUJI-PAUDAL (Japan). For obtaining microspheres or beads from the extruded product provided in the form of spaghetti, an apparatus called "spheronizer" (CALEVA Great-Britain) or MARUMERIZER (FUJIU-PAUDAL Japan) type is used.

Another conventional technique for obtaining beads consists in spraying and/or dusting cores obtained through agglomeration of the Diltiazem or salt thereof, such as the chlorohydrate, contingently mixed to at least a wetting agent, with a dispersion or solution of at least one wetting agent, for example in a known pilling turbine or in a granulating apparatus, such as the CF granulator system of FREUND INDUSTRIAL CO. (Japan), or in a known planetary granulator such as the collette (Belgium) type.

The obtained beads are dried by any means, for example in an oven or by means of a gas in a fluidized bed.

Finally, said beads are calibrated to the necessary diameter by passage through appropriate screens.

A pasty or plastic mixture, appropriate to be granulated by means of anyone of the above described techniques, may contain the following weight proportions of the Diltiazem or salt thereof, wetting agents and carriers or excipients:

20 to 85%; Diltiazem hydrochloride 2 to 20% sucroesters WE 15 (wetting agent);

5 to 25% Avicel PH 101 (microcrystalline cellulose of FMC, U.S.A.);

2 to 10% Methocel E 5 (hydroxypropylmethylcellulose of DOW, U.S.A.);

1 to 15% polyvinylpyrrolidone and 5 to 40% distilled water.

Said microporous membrane may be applied onto said beads by pulverizing an aqueous solution or dispersion of at least one of the above-named polymers and at least one of the above-mentioned adjuvants onto said beads. This pulverization may be carried out by spray-gunning or by pulverizing the above-named dispersion into a turbine or fluidized bed.

Generally, the present extended release form composition of Diltiazem salt is administered orally. The dosage amount is subject to the response of the individual patient, however, in general, from about 120 mg to about 480 mg per day of Diltiazem salt is administered per day per patient in total.

Additionally, the extended release form composition of the present invention may include other pharmaceutically active ingredients than the Diltiazem salt, provided that the other active ingredient is not pharmaceutically incompatible with the Diltiazem salt.

For example, other pharmaceutically active ingredients, such as β-adrenoceptor blocking agents or diuretics may be used in the present compositions. However, these are only example and are not intended to be limitative.

As examples of β-adrenoceptor blocking agents, drugs such as Propranolol, Atenolol, Labetalol, Prindolol or Sotalol may be used, for example.

As examples of diuretic agents, drugs such as Hydrochlorothiazide, Furosemide, Ethacrynic Acid or Chlorothiazide, for example.

Further, the additional associated drugs may be present in extended-release form also, if desired, however, they need not be.

The present invention will now be further illustrated by reference to certain examples which are provided solely for purposes of illustration and are not intended to be limitative.

According an illustrative embodiment of the present invention, said microporous membrane may be obtained, starting from an aqueous dispersion which contains by weight:

10 to 70 Eudragit E30D (polymer)
0.5 to 15% talc (lubricant)
0.5 to 15% Titanium dioxide (lubricant)
0.5 to 15% Magnesium stearate (lubricant)
0.5 to 15% polyvinylpyrrolidone (plastifying agent)
0.01 to 2% silicone oil (antifoaming agent);
0.05 to 5% polysorbate 80 (wetting agent)
10 to 70% water (carrier)

EXAMPLES

The present invention will now be further illustrated by reference to certain examples, which are provided solely for purposes of illustration and are not intended to be limitative. In particular, examples are provided for Diltiazem Hydrochloride extended release galenic forms, a process for preparing the same, therapeutic applications therefor and pharmacokinetic controls using the present galenic forms.

EXAMPLE 1

Beads Manufacture

| | |
|---|---|
| Diltiazem hydrochloride | 1120 g |
| Lactose | 119 g |
| Microcrystalline cellulose (Avicel pH 101) | 140 g |
| Povidone k 30 | 21 g |

After introducing the powders into a planetary mixer and granulating same though the obtained plastic mass is extruded through a cylinder with 1 mm diameter holes (Alexanderwork). The small cylinders are rounded, so as to obtain beads, by means of a spheronizer. After drying at 60° C. for 12 hours the beads are sifted and the fraction with size comprised between 0.7 mm and 1.4 mm are retained. 1,179 g of beads were obtained yield (84%).

EXAMPLE 2

| | |
|---|---|
| Diltiazem Hydrochloride | 560 g |
| Crodesta F 160 | 59.5 g |
| Microcrystalline cellulose (Avicel pH 101) | 70 g |
| Povidone k 30 | 10.5 g |

The ingredients are introduced in a planetary mixer and dry mixed during approximately 15 minutes. Thereafter 100 ml water USP is added and the mixing is pursued during 10 minutes more until a plastic mass is obtained. This mass is then extruded through a Fuji Paudal extruder equipped with a 1 mm screen so as to obtain "spagetties". A spheronizer type caleva is used so as to transform the extruded product in beads. After drying during 12 hours, on trays, in an oven at 60° C the beads are sieved so as to eliminate the ones with a size larger than 1.4 mm and with a size smaller than 0.7 mm. The amount of beads obtained with size comprised between 0.7 mm and 1.4 mm was 639.1 g (yield 91.3%).

EXAMPLE 3

Beads prepared in Example 1 were a STREA-1 (Aeromatic) fluidized bed using the "Top spraying" technic. 440 g of coating suspension of the following composition was applied on 500 g of beads. Thereafter the coated beads were dried at 50° C. during 16 hours.

| Coating suspension composition: | |
|---|---|
| Magnesium stearate | 12.5 g |
| Titanium dioxide | 5.0 g |
| Povidone k 30 | 5.0 g |
| Eudragit NE30D | 620.0 g |
| Talc USP | 17.5 g |
| water | 338.0 g |
| Simethicone | 1.0 g |
| Tween 80 | 0.8 g |

"In vitro" dissolution were obtained using the apparatus #2 as described in the United States Pharmacopeia. The 900 ml dissolution medium consisted of a phosphate butter pH 5.8 and the revolution speed 100 rpm.

| elapsed time [h] | percent dissolved [%] |
|---|---|
| 1 | 5 |
| 4 | 34 |
| 8 | 62 |
| 12 | 84 |

EXAMPLE 4

The beads as in Example 2 were coated using a fluidized bed coater equipped with a "wurster" system. 8 kg of uncoated beads were introduced in an Aeromatic Aerocoater and 2.77 kg of the following coating suspension was applied at a rate of 30–35 g per minute. Thereafter the coated beads were dried during 15 hours at 45° C.

| Coating suspension: | |
|---|---|
| Magnesium stearate | 0.636 kg |
| Talc | 0.636 kg |
| Titanium dioxide | 0.0909 kg |
| Hydroxypropylmethylcellulose | 0.200 kg |
| Polysorbate 80 NF | 0.007 kg |
| Simethicone c emulsion | 0.018 kg |
| Eudragit NE 30 D | 12.4 kg |
| purified water | 6.7 kg |

Dissolution "In Vitro"

The results were obtained using the same equipment as in Example 3. The dissolution medium was composed of 900 ml of water and the temperature was maintained of 37°±0.5° C.

| elapsed time [h] | percent dissolved [%] |
|---|---|
| 2 | 9 |
| 4 | 33 |
| 6 | 54 |
| 8 | 82 |

Pharmacokinetical Results

The new galenic form of Example 4 was the object of a pharmacokinetical study in comparison with a form in accordance to the prior art as described in U.S. Pat. No. 4,721,619. (Cardizen SR ®) therefore 6 healthy subject received successively in a random order 300 mg of each of the 2 products. The product of Example 4 was administered at a dose of 300 mg once daily while the product on the market was administered twice daily at a dose of 150 mg (300 mg daily total dose) during 7 days. At each of the eight day, 1 samples of blood were withdrawn when product of Example 4 was administered and 15 blood samples where withdrawn after the Cardizen SR ® administration. Diltiazem plasma levels were assayed using a specific high pressure liquid chromatographic method. FIG. 1 shows the results obtained: the continuous line represent the Diltiazem plasma levels obtained with the product of Example 4 and the broken line the Diltiazem plasma levels of Cardizen SR ®.

FIG. 1

| Pharmacokinetical parameters: | | | |
|---|---|---|---|
| | Units | Example 4 | Cardizen SR ® |
| Area under the curve [0–24 h] | mg.h/ml | 2782 ± 1037 | 2864 ± 1222 |
| Maximal concentration | mg/ml | 116.3 ± 54.1 | 192.7 ± 85.3 |
| Time of maximum concentration | h | 8.0 ± 1.8 | 5.2 ± 2.8 |
| Fluctuation | % | 85.7 ± 25.7 | 109.5 ± 25 |
| Time during the concentration is above 75% of the maximum concentration | h | 9.8 ± 2.3 | 6.7 ± 3.7 |

From these results the following conclusion can be drawn:

First, FIG. 1 shows that the Diltiazem plasma levels obtained after a once daily administration of one of the products of the present invention are comparable to the ones obtained after a twice daily administration of the product of the previous art.

Second, the bioavailability, expressed by the areas under the curve of the 2 products, is equivalent (no statistical detectable difference).

Third, the maximal concentration and the fluctuations obtained after a once daily administration of the product of the present invention is lower than the one obtained with Cardizen SR ® after a twice daily administration.

Fourth, the time during the concentration is above 75% of the maximum concentration is 46% longer after the once daily administration of the product of the present invention than with product of the previous art when given twice daily.

Food Effect Study

The product of Example 4 was given to 24 healthy volunteers and the bioavailability was measured after single oral dose of 300 mg given with and without food.

Figure 2:
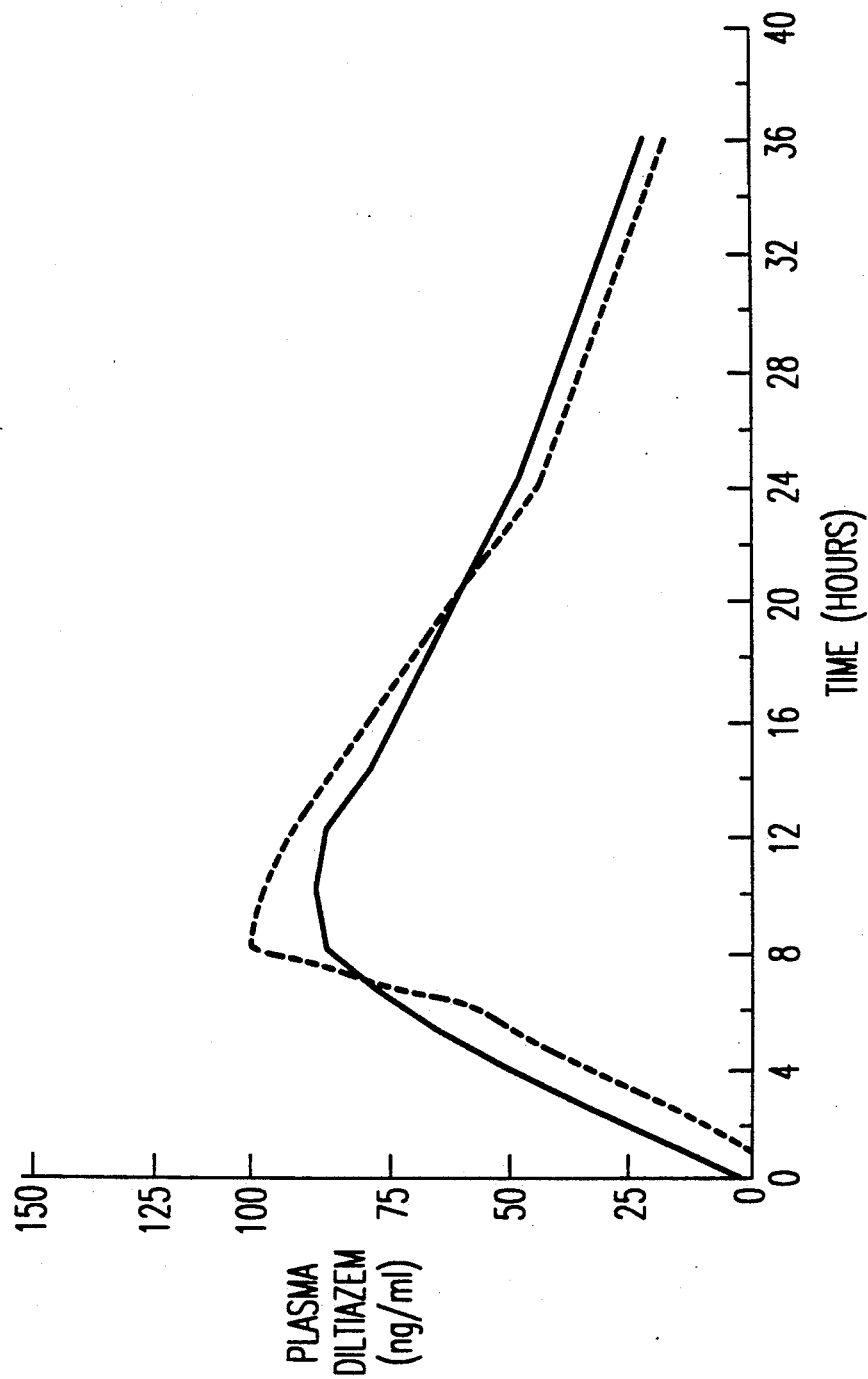
FIG. 2 illustrates in the solid curve, the mean plasma levels obtained when the product of the present invention is taken without food. The dotted curve represents mean plasma levels obtained when the product is taken with food.

The clinical trial was conducted as an open, single dose, randomized, cross over study. Blood samples were obtained before and until 36 hours after the administration. The experiment was repeated in the same subjects with the other treatment at an interval of 7 days. The plasma concentration of Diltiazem was determined in all available samples using an HPLC method. Pharmacokinetics parameters were derived from the individual plasma concentration versus time profiles and statistically compared for treatment differences and assessment of bioequivalence. FIG. 2 curves shows the mean plasma levels obtained when the product is taken without food and the dotted curve the mean plasma levels obtained when the product is taken with food.

FIG. 2

| Pharmacokinetics parameter - product of Example 4 | | | |
|---|---|---|---|
| | Units | Fasting | Food |
| Area under the curve (total | mg.h/ml | 1988 ± 119 | 1925 ± 109 |
| Mean residence time | h | 21.3 ± 0.7 | 19.9 ± 0.9 |
| $K_a$ | $h^{-1}$ | 0.283 ± 0.024 | 0.300 ± 0.027 |
| Maximum concentration | mg/ml | 100 ± 4.8 | 112 ± 5.9 |

No statistical difference was detectable. The product of Example 4 given with food is bioequivalent to the administration without food to within less than 20% regarding area under the curve, mean residence time and maximum concentration. The larger interval obtained for $K_a$ was due to the higher variability of this parameter, the difference between the treatment means remaining small (6.%).

From all the results it appears clearly that the product of the present invention can be administered once a day and that the plasma concentration variations are lower than the one obtained with the conventional product given twice a day.

Having described the present invention, it will now be apparent to one skilled in the art that many changes and modifications may be made to the above-described embodiments while remaining within the spirit and the scope of the present invention.

What is claimed as new and desired to be secured by Letters Patent of the United States is:

1. An extended-release galenical composition of Diltiazem or one or more pharmaceutically-acceptable salts thereof, which comprises beads, said beads consisting essentially of in admixture together:
a) an effective amount of Diltiazem or said one or more salts thereof as an active ingredient, and
b) an effective amount of a wetting agent, wherein said wetting agent is selected from the group consisting of a sugar, a $C_{12}$–$C_{20}$ fatty acid ester of sucrose or xylose, a glyceride of sucrose, a fatty acid ester of polyoxyethylene, an ether of fatty alcohols and polyoxyethylene, an ester of sorbitan, an ester of polyoxyethylene sorbitan, a glyceride-polyglycide, an alcohol-polyglycide ester, lecithins and a combination thereof,
wherein said beads are coated with a microporous membrane constituted by an aqueous dispersion of a neutral copolymer of ethyl acrylate and methyl acrylate, and a pharmaceutically-acceptable adjuvant.

2. The extended-release galenical composition of claim 1, wherein said salt is the hydrochloride salt.

3. The extended-release galenical composition of claim 1, wherein the weight of the microporous membrane is about 2 to 35% by weight of that of the uncoated beads.

4. The extended-release galenical composition of claim 3, wherein the weight of the microporous membrane is about 5 to 22% by weight of that of the uncoated beads.

5. The extended-release galenical composition of claim 1, wherein the weight of the Diltiazem salt is about 20 to 95% by weight.

6. A pharmaceutical composition, comprising an extended-release galenical composition of Diltiazem or one or more pharmaceutically-acceptable salts thereof, which comprises in capsule form:
a) beads consisting essentially of an effective amount of each of Diltiazem or said one or more salts thereof and a wetting agent in admixture together, wherein said wetting agent is selected from the group consisting of a sugar, a $C_{12}$–$C_{20}$ fatty acid ester of sucrose or xylose, a glyceride of sucrose, a fatty acid ester of polyoxyethylene, an ether of fatty alcohols and polyoxyethylene, an ester of sorbitan, an ester of polyoxyethylene sorbitan, a glyceride-polyglycide ester, an alcohol-polyglycide ester, lecithins and a combination thereof,
wherein said beads are coated with a microporous membrane constituted by an aqueous dispersion of a neutral copolymer of ethyl acrylate and methyl methacrylate, and a pharmaceutically-acceptable adjuvant, and
b) one or more other pharmaceutically active ingredients which are pharmaceutically compatible with Diltiazem or said one or more salts thereof.

7. The pharmaceutical composition of claim 6, wherein said one or more other pharmaceutically active ingredients comprise-$\beta$-adrenoceptor or diuretic compounds or compositions containing the same.

8. The pharmaceutical composition of claim 6, wherein the weight of the microporous membrane is about 2 to 35% by weight of that of the uncoated beads.

9. The pharmaceutical composition of claim 6, wherein said salt is the hydrochloride salt.

10. The pharmaceutical composition of claim 6, wherein the weight of the microporous membrane is about 5 to 22% by weight of that of the uncoated beads.

11. A method for treating angina pectoris or hypertension or both in a mammal, which comprises administering to said mammal an effective amount of an extended-release galenical composition consisting essentially of Diltiazem or one or more pharmaceutically-acceptable salts thereof and a wetting agent in admixture together in the form of beads, wherein the wetting agent is selected from the group consisting of a sugar, a $C_{12}$–$C$·fatty acid ester of sucrose or xylose, a glyceride of sucrose, a fatty acid ester of polyoxyethylene, an ether of fatty alcohols and polyoxyethylene, an ester of sorbitan, an ester of polyoxyethylene sorbitan, an alcohol-polyglycide ester, a glyceride-polyglyceride lecithins and a combination thereof, and
wherein the beads are coated with a microporous membrane constituted by an aqueous dispersion of a neutral copolymer of ethyl acrylate and methyl methacrylate, and a pharmaceutically-acceptable excipient.

12. The method of claim 11, wherein said administration is orally and once per day.

13. The method of claim 11, wherein said mammal is a human.

14. The method of claim 12, wherein from about 120 mg to about 480 mg of said one or more Diltiazem salts are administered in total per day.

15. The method of claim 11, wherein said salt is the hydrochloride salt.

* * * * *